United States Patent [19]

Brolund

[11] Patent Number: 5,344,943
[45] Date of Patent: Sep. 6, 1994

[54] LONG-CHAIN KETENE DIMERS

[75] Inventor: Nils Brolund, Duren, Fed. Rep. of Germany

[73] Assignee: Akzo Nobel N.V., Netherlands

[21] Appl. No.: 998,810

[22] Filed: Dec. 29, 1992

[30] Foreign Application Priority Data

Dec. 30, 1991 [EP] European Pat. Off. ......... 91203425.3

[51] Int. Cl.$^5$ ............................................ C07D 305/12
[52] U.S. Cl. ..................................................... 549/329
[58] Field of Search ......................................... 549/329

[56] References Cited

U.S. PATENT DOCUMENTS 2,369,919  2/1945  Sauer .................................... 260/550

FOREIGN PATENT DOCUMENTS

| 748980 | 12/1944 | Fed. Rep. of Germany | 549/329 |
|---|---|---|---|
| 2327988 | 1/1975 | Fed. Rep. of Germany | 545/329 |
| 2335488 | 2/1975 | Fed. Rep. of Germany | 549/329 |
| 2927118 | 1/1981 | Fed. Rep. of Germany | 549/329 |
| 3434212 | 3/1985 | Fed. Rep. of Germany | 549/329 |

OTHER PUBLICATIONS

European Search Report, dated Sep. 7, 1992.

Chenmical Abstract, vol. 117, Abstract No. 7788f (1992).

*Primary Examiner*—James H. Reamer
*Attorney, Agent, or Firm*—Ralph J. Mancini; Louis A. Morris

[57] ABSTRACT

Long-chain ketene dimers are prepared in a process in which in the absence of an organic solvent, carboxylic acid chloride is fed, with intensive mixing, into a recipient of triethyl amine at a rate of not more than 3 moles/-hour per mole of present triethyl amine, and the mixing rate, feed rate, and heat exchange are so attuned to each other that the viscosity of the mixture always is less than 250 mPa.s, measured at 60° C. (rate of shear higher than 100 1/sec). The process is characterized in that the molar ratio of the total amount of carboxylic acid chloride fed in to the recipient amount of amine is 1:1.025 to 1:2, and, after the conversion, the reaction mixture containing the ketene dimer is treated with diluted aqueous hydrochloric acid or an aqueous solution of triethyl amine hydrochloride and hydrochloric acid, and the ketene dimer is separated. The ketenes prepared in accordance with the present invention are highly suitable for use in paper sizing.

11 Claims, No Drawings

LONG-CHAIN KETENE DIMERS

FIELD OF THE INVENTION

The invention relates to long-chain ketene dimers derived from saturated or unsaturated carboxylic acids, a process for the preparation of same, and the use thereof as a sizing agent for paper.

BACKGROUND OF THE INVENTION

Ketenes can be perceived as inner anhydrides of carboxylic acids. Most ketenes dimerise or are stable only as dimers, such as the ketenes which derive from higher fatty acids.

Generally, these ketene dimers are prepared by reacting corresponding carboxylic acid chlorides with tertiary amines, more particularly triethyl amine. The course of reaction, as represented for example by the reaction of lauric acid chloride with triethyl amine, may be depicted as follows.

$$2C_{10}H_{21}-CH_2-COCl + 2(C_2H_5)_3N$$

$$2(C_2H_5)_3N \cdot HCl + 2[C_{10}H_{21}-CH=C=O]$$

$$C_{10}H_{21}-CH=C-O$$

$$C_{10}H_{21}-CH-C=O$$

$$2(C_2H_5)_3N \cdot HCl + 2NaOH \rightarrow 2(C_2H_5)_3N + 2NaCl + 2H_2O$$

The intermediarily formed ketene immediately dimerises into a diketene. The amine can be recovered from the amine hydrochloride formed as by-product by mixing an aqueous solution of the hydrochloride with sodium hydroxide solution and separating the organic phase which forms.

During the mixing of triethyl amine and fatty acid chlorides the viscosity rises very rapidly to high values because the crystalline growth of the triethyl amine hydrochloride precipitating under reaction conditions which is above all a dendritic growth, and prevents active stirring and hence the removal of the released reaction heat. Thus, to reduce and control the viscosity it was necessary up till now to carry through the conversion in an inert organic solvent.

U.S. Pat. No. 2,369,919 describes a process in which comparatively strongly diluted fatty acid chloride dissolved in an anhydrous solvent such as benzene or ether, is presented and mixed with the tertiary amine. The amine hydrochloride formed precipitates and must be separated by suction from the organic solution in which it is present as a very particulate suspension. The drawback to this process is that working with organic solvents, the recovery of which is expensive and time-consuming; moreover, working with organic solvents is always attended with hazards for fellow workers and the environment. Also, losses of solvents and product will occur, for instance when working up the filter cake.

DE-OS 2 327 988 discloses a process in which the amine hydrochloride is separated by briefly washing it with a diluted solution of neutral salt, e.g. with a 10% solution of sodium sulphate. However, in this process also a water-immiscible organic solvent is employed. Besides, using sodium sulphate means the introduction into the process of a further chemical substance, which likewise must be worked up again or disposed of.

Mixing the suspension with carboxylic acids such as formic acid, acetic acid, and the like, as can be inferred from DE-OS 2 35 488, is attended with similar drawbacks.

Frequently, the purity of ketenes obtained in this way is not satisfactory; thus DE-OS 2 927 118 recommends carrying out the conversion of the fatty acid chloride with a mixture of trimethyl amine and some other tertiary amine. Although the use of two tertiary amines leads to a partial reduction of the reaction viscosity, nevertheless this process also requires inert solvents to control the viscosity of the intermediate product. Hence, this process is also attended with the drawbacks already mentioned above because use has to be made of organic solvents.

Finally, DE-OS 3 434 212 does not describe an essentially different process either, since instead of the otherwise used organic solvent it employs melted wax, which, ultimately, is likewise an organic solvent. Admittedly, this wax does not have to be removed, since it can be used together with the diketene in special paper sizing processes. However, it is not possible to prepare diketenes in the pure form according to this process.

Although many processes for the preparation of long-chain ketene dimers are already known, the need for enhanced preparative processes remains.

It is therefore the object of the invention to provide a process which is not affected by the disadvantages outlined above and, in particular, works without the use of an organic solvent which must be recovered and purified, can be carried through in a commercially and technically advantageous manner, is environment-friendly, and does not yield any additional by-products which must be disposed of or will appear as impurities in the production waste water.

SUMMARY OF THE INVENTION

The present invention generally relates to a process for the preparation of long-chain ketene dimers. The process comprises reacting carboxylic acid chlorides of the formula $RCH_2COCl$, wherein R is a saturated or unsaturated hydrocarbon group having 6–30 carbon atoms, with a tertiary amine in the absence of an organic solvent to obtain ketene dimer/amine hydrochloride-containing mixture. The present process is characterized in that in the absence of an organic solvent carboxylic acid chloride is fed, with intensive mixing, into a recipient of triethyl amine at a rate of not more than 3 moles/hour per mole of present triethyl amine, and wherein the mixing rate, feed rate, and heat exchange are so attuned to each other that the viscosity of the mixture always is less than 250 mPa.s, measured at 60° C. (rate of shear higher than 100 1/sec), and the molar ratio of the total amount of carboxylic acid chloride fed in to the recipient amount of amine is 1:1.025 to 1:2. After the conversion, amine hydrochloride containing the reaction mixture containing ketene dimer is treated with diluted aqueous hydrochloric acid or an aqueous solution of triethyl amine hydrochloride and hydrochloric acid, and the ketene dimer is separated.

DETAILED DESCRIPTION OF THE INVENTION

The present invention is directed to a process for the preparation of long-chain ketene dimers without the use of an organic solvent. The process comprises reacting carboxylic acid chlorides of the formula:

$$RCH_2COCl$$

wherein the R is a saturated or unsaturated hydrocarbon group having 6–30 carbon atoms, with a tertiary amine, without need for an organic solvent to obtain a amine hydrochloride-containing mixture containing ketene dimer. The amine-hydrochloride containing mixture is then treated with dilute aqueous hydrochloric acid or an aqueous solution of triethyl amine hydrochloride and hydrochloric acid to separate out the ketene dimer product.

Preferred tertiary amines are trialkyl amines. In a preferred embodiment, triethyl amine is employed.

In a particularly advantageous embodiment of the process according to the invention the carboxylic acid chloride is fed into the recipient triethyl amine at a rate of not more than 1 mole/hour per mole of present triethyl amine. On conclusion of the feeding an after-reaction time may be adhered to, e.g. of 5 to 30 minutes, more particularly 10–20 minutes. The conversion is conveniently carried out at a temperature in the range of 50° to 100° C., more particularly in the range of 55°–65° C. The treatment of the amine hydrochloride containing reaction mixture is best carried out with an aqueous solution containing 0–50 wt. % of triethyl amine hydrochloride and 3–32 wt. %, preferably 4–6 wt. % of hydrochloric acid The separation of the aqueous phase from the ketene can take place, int. al., through sedimentation or centrifuging. The obtained ketene may be dried by means of countercurrent drying, e.g. with dry nitrogen. The amine hydrochloride may be treated in a conventional manner with, say, sodium hydroxide solution to recover the amine. In a further advantageous embodiment the process according to the invention is carried out continuously, with the starting components being continuously fed into an agitator vessel or a loop reactor for carrying out the main reaction, and the after-reaction being carried out in a tubular reactor connected thereto at the outlet side.

It is preferred that the acid chloride be fed into said triethyl amine under intensive mixing at a rate of not more than 3 moles/hour per mole of triethyl amine, and mixing, feed rate and heat exchange are controlled such that the viscosity of the mixture is maintained at less than about 250 mPa.s, measured at 60° C. (rate of shear higher than 100 1/sec) and the molar ratio of the total amount of carboxylic acid chloride fed into the triethyl amine is 1:1.025 to 1:2.

The invention further relates to the ketene dimers obtained by the process according to the invention. The invention also relates to the use of the ketenes as sizing agent for paper.

Generally, a vessel equipped with an effective stirrer and internal and external heat exchangers is provided to carry out the process according to the invention. Also to be provided are inlets for the separate dosing of the starting substances, an outlet for discharging the reaction mixture and devices for measuring the existing temperature, pressure, and viscosity. It is required to employ a highly effective stirrer adapted to the mixing problem, such as an appropriately constructed anchor agitator, in order to ensure sufficient backmixing in the reaction medium and heat transfer ratios for the discharge of the enthalpy of reaction.

After conversion, the reaction mixture composed of triethyl amine, triethyl amine hydrochloride, and ketene dimer is treated with diluted aqueous hydrochloric acid or an aqueous solution of hydrochloric acid and triethyl amine hydrochloride to neutralize the excess amine and extract the crystalline product TEA.HCl from the mixing phase. Preferably, the reaction mixture is poured into the acid solution or the acid salt solution with stirring. The amount of hydrochloric acid used is as much as is required to remain always in the acid pH range of the aqueous solution.

Particularly surprising was that using the process according to the invention, it is possible to work without an organic solvent from the beginning of the process to its end. By adhering to the process conditions and controlling them, dendritic growth of the amine hydrochloride crystals can successfully be prevented and the crystal formation steered primarily in the direction of hexagonal prismatic crystals.

Since there is no need to build up a filtercake of amine hydrochloride as is the case in processes using organic solvents, the losses of ketenes which cling to the filtercake together with the solvent residues then are canceled.

The obtained ketene is free of residues of organic solvent and contains only a minor quantity of product-typical impurities such as fatty acid anhydrides and fatty acids.

Moreover, besides the main product in the present process, only NaCl is formed as by-product from the triethyl amine recovery, and this can be disposed of without any problem as purified salt solution. Pollution of the environment by organic solvent residues is precluded.

The separation of the ketene dimer and the further working up/purification thereof can be carried out in a simple manner.

The invention will be further illustrated with reference to the following non-limiting examples.

EXAMPLE 1

Prparation of an alkyl diketene (AKD) in batch operation a. Reaction apparatus

A cylindrical agitator vessel with thermostatable jacket and an effective capacity of 1 l ($\phi \times$ h: 10 * 14 cm) was equipped with an anchor agitator reaching to the inner wall. The anchor agitator in its typical design covers the entire bottom surface and the whole 14 cm cylinder height of the reaction apparatus. Also installed were a thermometer attached at half the inner radius, a continuously functioning feeding device for organic acid chlorides in the agitator vessel, and a reflux condenser with superimposed Bunsen valve. For heating and cooling the reactant were used a commercially available 2 kW circulation thermostat with a liquid volume of 5 l and an external heat exchanger. The transport of the heat carrier medium between the thermostat and the double jacket of the reaction vessel was effected via the thermostat's internal pump.

b. Synthesis work cycle

To carry out the synthesis 230.1 g (2.27 moles) of triethyl amine (hereinafter referred to as TEA) with a maximum residual water content of 0.2 wt. % were put into the agitator vessel and thermostated at 60° C. The anchor agitator was fixedly set at a speed of rotation of 300 rpm, thus attaining a typical circumferential speed of about 1.6 m/sec.

After the reactor temperature of 60° C. was reached, dosing was started of in all 614.3 g (2.08 moles) of palmitoyl chloride/stearoyl chloride (average molecular weight: 296 g/mole; hereinafter referred to as FAC), which was added via a feed pump in a constant volume flow over a period of precisely 60 minutes.

The forming of AKD and its main by-product, triethyl amine hydrochloride (hereinafter referred to as TEA*HCl), took place almost instantly and manifested itself in the spontaneous clouding of the TEA phase and an increase in temperature in the reaction vessel of about 2°–3° C. With the incorporation of the FAC dosing the temperature of the heat exchanger medium conveniently was reduced about 5°–6° C. vis-a-vis the temperature of the reaction medium, as a result of which, under the given heat transfer conditions, a sufficient driving force for temperature drop for this apparatus was formed. After about 5 minutes an internal temperature of 60° C. was attained in equilibrium condition. As the FAC dosing proceeded, the viscosity of the reaction mixture steadily increased, reaching a dynamic viscosity of 250 mPa.s (60° C., d > 100 1/sec) at the end of the reaction. The measurements were carried out on the end products individually in a Haake RHEOCORD 20 with a cone and plate system; the rate of shear of d > =100 1/sec corresponded to the conditions of free flow through pouring out or slow stirring. After the FAC addition had been concluded, an after-reaction time of 15 minutes at 60° C. with continued stirring was adhered to.

In all, 845.2 g of solids suspension of TEA*HCl in AKD were obtained, with a regulatory residual portion of 10 mole % excess of free TEA per mole of dosed FAC. The suspension can be taken for further working up by means of purging through the bottom valve of the reactor or by being poured from the reactor.

c. Working up

The treatment of the crude product described hereinbelow may serve either to obtain a sample for analytical characterization, or as a basis for scaled-up separation and purification operations.

In a 400 ml beaker (high shape) with an internal thermometer, 77 g of aqueous HCl of 4.7 wt. % were heated to 60° C. A dissolver stirrer of appropriate size was placed about 1 cm above the beaker bottom and set to about 800 rpm, and an aliquot prepared at 60° C. of 204 g of the reaction product described in section 2 was speedily added to the aqueous phase. Because of the neutralization heat of the free amine the temperature will rise rapidly, depending on the rate of addition of the suspension, and if desired can be so regulated that 70° C. is not exceeded. On conclusion of the addition stirring was continued for 5 minutes, after which the two-phase mixture was transferred to a thermostatable separating funnel for deposition at 60°–65° C. After the passing of 15 minutes the AKD upper phase and the slightly cloudy TEA*HCl lower phase had separated sufficiently and were discharged one after the other. Obtained were 133.7 g of crude AKD and 147.3 g of aqueous TEA*HCl solution.

The organic fat phase was then transferred to a round-bottom flask and dried in a rotation evaporator at 65° C. under water jet vacuum for 15–30 minutes. A drying loss of 1.02 g (0.76 wt. %) was obtained as a result of the removal of water. The drying process can be speeded up considerably by passing through dry nitrogen.

The amine salt crystallized out through the removal of water and still containing AKD can then be removed by means of suitable filtration steps. In this way 0.95 g TEA*HCl (0.71 wt. %) were separated.

d. Analytical characterization

The proportion of AKD contained in the product was determined in a known manner by means of morpholine titration and adjusted to the free fatty acid content. As a further characteristic magnitude the acid number, which was determined in accordance with ASTM D 974-64, was taken into consideration.

The AKD wax characterized by these methods had an AKD content of 90.5% and an acid number of 7 mg KOH/g.

e. Remarks on the crystalline structure of TEA*HCl

Measurements by light-optical microscope on samples of the formed TEA*HCl crystals, which were made at 10-minute intervals as the reaction proceeded, initially show the acicular structure typical for this product ($\phi$1-2 $\mu$m, L 20–100 $\mu$m). The wear taking place in the course of the reaction, however, leads to a reduction of the crystal size, as a result of which the average length is reduced to about 30 $\mu$m. Contrary to the usual experience, the further crystal growth takes place with regular hexagonal prisms being formed, which are especially noticeable for their decidedly compact shape and the absence of dendritic side branches. On average, at the end of the reaction crystals with an average length of 20–40 $\mu$m and a diameter of 5–10 $\mu$m were obtained.

EXAMPLE 2

Preparation of AKD in continuous operation with a two-step agitator vessel cascade a. Reaction apparatus An agitator vessel (1 l) constructed and dimensioned as in Example 1 was connected in cascade with a similar apparatus with an effective capacity of 250 ml. As stirrer in the second cascade reactor was used an anchor agitator of the same design and arrangement but adapted to the spatial conditions. The two reactors had a double-jacket construction, and were connected in series for heating and cooling. Also, installed at half the inner radius of the reactors were an internal thermometer and a continuously functioning feeding device for organic acid chlorides and triethyl amine, respectively, and a reflux condenser with superimposed Bunsen valve. For heating and cooling the reactant use was made of a commercially available 2 kW circulation thermostat with a liquid volume of 5 l and an external heat exchanger. The transport of the heat carrier medium between the thermostat and the double jacket of the reaction vessel was effected via the thermostat's internal pump.

The required transport of substance between the two cascade vessels takes place via a controllable gear pump kept at 60° C. The discharge from the second vessel is so controlled by the appropriate setting of the bottom discharge valve that the filling level was kept at its designated height.

b. Synthesis work cycle 230.1 g (2.27 moles) of TEA were charged into the first cascade vessel and brought to a reaction temperature of 60° C. After the rotational speed of the stirrer had been set at 300 rpm, the dosing was started, as in Example 1, of 614.3 g (2.08 moles) of FAC, the rate of feeding being so regulated that the indicated amount was completely transferred to the first reactor in 60 minutes. Immediately on conclusion of the single feeding of FAC, the dosing of TEA to the first reactor was connected up and so regulated, that within 60 minutes 230.9 g (2.28 moles) of TEA were passed to the reactor.

The (rising) liquid level was then kept at its nominal level by appropriate setting of the gear pump and dosing to the second reactor. For rapid filling of the second reactor its bottom valve remained closed in the starting phase and only after the nominal filling level of 250 ml at 60° C. had been reached was it opened so far as to give an equilibrium condition.

The indicated dimensioning of reactors, filling quantities, and throughputs of FAC and TEA yielded, in equilibrium condition, reaction volumes of 1 l in the first reactor at the reaction temperature, and of 250 ml in the second reactor, from which average dwelling times of 60 minutes and 15 minutes, respectively, were derived.

c. Synthesis result

To determine the conversion of FAC/TEA into AKD, a sample of the reaction mixture was taken at the outlet of the second reactor in the conventional manner after at least four residence periods in the main reactor, which sample was then worked up and characterized as described in Example 1, items 3-4.

An AKD wax obtained according to this example had an AKD content of 91.5% and an acid number of 10 mg KOH/g.

EXAMPLE 3

Preparation of AKD in continuous operation with a cascade composed of a loop reactor and an agitator vessel a. Reaction apparatus An agitator vessel constructed and dimensioned as in Example 2 (1 l) (cascade vessel no. 1) was connected in series with a laminar driven tubular reactor with an effective capacity of 375 ml ($\phi$ internally 9 mm). The tubular reactor had a double-jacket construction and was connected in series with the double jacket of the agitator vessel for thermostating. To maintain the nominal filling level in the agitator vessel the reactors were effectively mutually disconnected by means of a controllable gear pump. The outlet of the tubular reactor was provided with a small swan neck to prevent it from emptying.

The remainder of the plant structure corresponds to the features as constructed in Example 2.

b. Synthesis work cycle 230.1 g (2.27 moles) of TEA were charged into the agitator vessel and brought to a reaction temperature of 60° C. After the rotational speed of the stirrer had been set at 300 rpm, the dosing was started of 614.3 g (2.08 moles) of FAC, the rate of feeding being so regulated that the indicated amount was passed to the agitator vessel in 60 minutes. Immediately on conclusion of the single feeding of FAC, the dosing of TEA to the first reactor was connected up and so regulated, that within 60 minutes 230.9 g (2.27 moles) of TEA were passed to the reactor. The liquid level in the vessel was then kept at its nominal level by appropriate setting of the gear pump and dosing to the connected tubular reactor.

The indicated dimensioning of reactors, filling quantities, and throughputs of FAC and TEA yielded, in equilibrium condition, reaction volumes of 1 l in the first reactor at the reaction temperature, and of 375 ml in the second reactor, from which average dwelling times of 60 minutes and 23 minutes, respectively, were derived.

c. Synthesis result

To determine the conversion of FAC/TEA into AKD, a sample of the reaction mixture was taken at the outlet of the second reactor in the conventional manner after at least four residence periods in the main reactor, which sample was then worked up and characterized as described in Example 1, items 3-4.

An AKD wax obtained according to this example had an AKD content of 92.5% and an acid number of 6 mg KOH/g.

EXAMPLE 4

Preparation of AKD in continuous operation using a loop reactor and a tubular reactor connected in series a. Reaction apparatus In divergence from Examples 1–3 use was made of a reaction loop of 380 ml ($\phi$ internally 11 mm) overall content equipped with a gear pump for circulating the reaction product and two spatially separated static mixers on the pressure side for homogeneous feeding of the reactants (FAC follows TEA). The reaction temperature was controlled by means of two PT100 detecting elements, which in each case were arranged upstream and downstream of the static mixers. Directly ahead of the intake ports of the circulation pump the loop branched out in a laminar driven tubular reactor with an effective capacity of 375 ml ($\phi$ internally 9 mm). Steps to disconnect pressure between the reactors, e.g. by means of regulating valves or forced feeding devices, did not prove necessary in this method of operation.

The reactants FAC and TEA were made available from storage containers and separately dosed into the loop for the respective static mixer via feed pumps.

The two reaction devices had a double jacket construction and were connected in series for thermostating by means of a circulation thermostat. The outlet of the tubular reactor was provided with a small swan neck to prevent emptying.

b. Synthesis work cycle

In divergence from the operation method used so far the loop was first filled completely with fresh AKD. This was conveniently done by taking melted AKD wax from a storage container and pumping it around the loop until bubbles were no longer to be determined therein. The AKD storage container was then disconnected and the circulation pumping of the AKD continued until the required reaction temperature of 60° C. had reached its state of equilibrium. Finally, the volume flow in the loop was set at 100 kg/hour or —taking into account the density of 860 kg/m3 of the mixture of AKD and TEA-HCl —at 116 l/hour.

Simultaneously, the dosing of FAC and TEA was connected up. The respective throughputs were 614.3 g/hour (2.08 moles) for FAC and 230.1 g (2.27 moles) for TEA. The reaction set in immediately, which was to be detected from the clouding of the wax phase. On account of the favorable surface-volume ratio of the reaction loop the discharge of heat gave hardly any problems, so that a decrease of the temperature of the thermostating liquid of only 1°-2° C. had to be dealt with.

Because of the pressure drop appearing in the loop, the reaction product after a few minutes independently passed into the tubular reactor and appeared for the first time at its outlet after some 23 minutes.

The indicated dimensioning of reactors, filling quantities, and throughputs of FAC and TEA yielded, in equilibrium condition, average dwelling times for the loop and the tubular reactor of 23 minutes in each case. A raising or lowering of the dwelling times is immediately obtainable by varying the throughput yield.

c. Synthesis result

To determine the conversion of FAC/TEA into AKD, a sample of the reaction mixture was taken at the outlet of the second reactor in the conventional manner after at least four residence periods in the main reactor, which sample was then worked up and characterized as described in Example 1, items 3–4.

An AKD wax obtained according to this example had an AKD content of 91.5% and an acid number of 8 mg KOH/g.

We claim:

1. A process for the preparation of long-chain ketene dimers which comprises reacting carboxylic acid chlorides of the formula:

wherein R is a saturated or unsaturated hydrocarbon group having 6–30 carbon atoms, with triethyl amine to obtain a amine hydrochloride-containing reaction mixture containing ketene dimer, and treating said mixture with dilute aqueous hydrochloric acid or an aqueous solution of triethyl amine hydrochloride and hydrochloride acid to separate out the ketene dimer product, wherein the process is characterized in that said acid chloride is fed, in the absence of an organic solvent into said triethyl amine under intensive mixing at a rate of not more than 3 moles/hour per mole of triethyl amine, and mixing, feed rate and heat exchange are controlled such that the viscosity of the mixture is maintained at less than about 250 mPa.s, measured at 60° C. (rate of shear higher than 100 1/sec) and the molar ratio of the total amount of carboxylic acid chloride fed into the triethyl amine is 1:1.025 to 1:2.

2. The process according to claim 1, wherein the carboxylic acid chloride is fed into the triethyl amine at a rate of not more than about 1 mole/hour per mole of present triethyl amine.

3. The process according to claim 1, wherein upon conclusion of feeding said acid chloride into said triethyl amine the mixture containing ketene dimer product is allowed to stand for 5–30 minutes.

4. The process according to claim 1, wherein the conversion is carried out at a temperature range of from about 50° to 100° C.

5. The process according to claim 1, wherein said treatment of the reaction mixture is carried out with an aqueous solution containing 0–50 wt. % of triethyl amine hydrochloride and 3–32 wt. % of hydrochloric acid.

6. The process according to claim 1, wherein the reaction of said organic fatty acid chlorides and triethyl amines is conducted in an agitator vessel in batch operation, and the separation of the ketene dimer product is carried out in batch operation, semi-continuous operation or continuous operation.

7. The process according to claim 1, wherein the reaction of said organic fatty acid chlorides and triethyl amines is conducted in an agitator vessel cascade in continuous operation, and the separation of the ketene dimer product is carried out in batch operation, semi-continuous operation or continuous operation.

8. The process according to claim 1, wherein the reaction of said organic fatty acid chlorides and triethyl amines is conducted in a combination of an agitator vessel and a tubular reactor in continuous operation, and the separation of the ketene dimer product is carried out in batch operation, semi-continuous operation or continuous operation.

9. The process according to claim 1, wherein the reaction of said organic fatty acid chlorides and triethyl amines is conducted in a combination of a loop reactor and a tubular reactor in continuous operation, and the separation of the ketene dimer product is carried out in batch operation, semi-continuous operation or continuous operation.

10. The process of claim 3 wherein said mixture is allowed to stand for about 10–20 minutes.

11. The process of claim 4 wherein said conversion is carried out at a temperature of from about 55° C. to 65° C.

* * * * *